US005843922A

United States Patent [19]
Whistler et al.

[11] Patent Number: 5,843,922
[45] Date of Patent: Dec. 1, 1998

[54] PREPARATION OF OLIGOSACCHARIDES AND PRODUCTS THEREFROM

[75] Inventors: Roy L. Whistler; James N. BeMiller, both of West Lafayette, Ind.

[73] Assignee: Fuisz Technologies Ltd., Chantilly, Va.

[21] Appl. No.: 662,201

[22] Filed: Jun. 11, 1996

Related U.S. Application Data

[63] Continuation of Ser. No. 282,807, Jul. 29, 1994, abandoned.

[51] Int. Cl.⁶ .......................... A61K 31/715; G07H 3/06; C12N 1/20
[52] U.S. Cl. .............................. 514/61; 514/54; 514/892; 536/124; 536/126; 536/4.1; 536/18.5; 426/650; 127/DIG. 1; 424/439; 424/442; 435/252.1
[58] Field of Search ................................... 536/4.1, 18.5, 536/124, 126; 514/54, 892, 61; 426/650; 127/DIG. 1; 424/439, 442; 435/252.1

[56] References Cited

U.S. PATENT DOCUMENTS

| | | | |
|---|---|---|---|
| 2,826,169 | 3/1958 | Le Veen | 54/79.4 |
| 2,918,404 | 12/1959 | Mende et al. | 514/683 |
| 3,019,745 | 2/1962 | Du Bois et al. | 425/9 |
| 3,036,532 | 5/1962 | Bowe | 425/9 |
| 3,067,743 | 12/1962 | Merton et al. | 424/431 |
| 3,070,045 | 12/1962 | Bowe | 425/9 |
| 3,073,262 | 1/1963 | Bowe | 425/9 |
| 3,095,258 | 6/1963 | Scott | 264/177.14 |
| 3,118,396 | 1/1964 | Brown et al. | 425/9 |
| 3,131,428 | 5/1964 | Mika | 264/177.13 |
| 3,308,221 | 3/1967 | Opfell | 264/174 |
| 3,324,061 | 6/1967 | Tanquary et al. | 264/211.17 |
| 3,482,998 | 12/1969 | Carroll et al. | 426/646 |
| 3,523,889 | 8/1970 | Eis | 210/713 |
| 3,557,717 | 1/1971 | Chivers | 426/660 |
| 3,595,675 | 7/1971 | Ash et al. | 426/576 |
| 3,615,671 | 10/1971 | Schoaf | 426/96 |
| 3,625,214 | 12/1971 | Higuchi | 424/424 |

(List continued on next page.)

FOREIGN PATENT DOCUMENTS

| | | |
|---|---|---|
| 609135 | 4/1988 | Australia . |
| 609137 | 4/1988 | Australia . |
| 900605 | 11/1977 | Belgium . |
| 1303511 | 4/1988 | Canada . |
| 2081246-6 | 4/1993 | Canada . |
| 2091641 | 9/1993 | Canada . |
| 0 287 488 A1 | 3/1988 | European Pat. Off. . |
| WO 88/08296 | 11/1988 | European Pat. Off. . |
| WO 88/08298 | 11/1988 | European Pat. Off. . |
| WO 90/0-6969 | 6/1990 | European Pat. Off. . |
| 0 387 950 A1 | 8/1990 | European Pat. Off. . |
| WO 90/11017 | 10/1990 | European Pat. Off. . |
| WO 91/07952 | 6/1991 | European Pat. Off. . |
| WO 92/06603 | 4/1992 | European Pat. Off. . |
| WO 92/20330 | 11/1992 | European Pat. Off. . |
| 0 540 460 A1 | 5/1993 | European Pat. Off. . |
| WO 93/08699 | 5/1993 | European Pat. Off. . |
| WO 93/11750 | 6/1993 | European Pat. Off. . |
| 0 561 735 A1 | 9/1993 | European Pat. Off. . |
| 93650010 | 9/1993 | European Pat. Off. . |
| 93650020 | 11/1993 | European Pat. Off. . |
| 86052 | 4/1988 | Israel . |
| 86053 | 4/1988 | Israel . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |
| 519858 | 5/1971 | Switzerland . |
| 489211 | 7/1986 | Switzerland . |
| 2 155 934 | 3/1985 | United Kingdom . |
| WO 91/18613 | 5/1991 | WIPO . |

OTHER PUBLICATIONS

R.H. Doremus, "Crystallization of Sucrose From Aqueous Solution," *Journal of Colloid and Interface Science*, 104, pp. 114–120 (1985).
P. Bennema, "Surface Diffusion and the Growth of Sucrose Crystals," *Journal of Crystal Growth*, 3,4 pp. 331–334 (1968).
T.D. Simpson, et al., "Crystalline Forms of Lactose Produced in Acidic Alcoholic Media," *Journal of food Science*, 47, pp. 1948–1954 (1982).
A.D. Randolph, et al., "Continuous Sucrose Nucleation," *The International Sugar Journal*, pp. 8–12 (1974).
K.B. Domvos, et al., "Methanol–Soluble Complexed of Lactose and of other Carbohydrates," *J. Dairy Science*, 43, pp. 1216–1223 (1960).
A.D. Randolph, et al., "Continuous Sucrose Nucleaton," *The International Sugar Journal*, pp. 35–38 (1974).
A.D. Randolph, et al., "Continuous Sucrose Nucleation," *The International Sugar Journal* pp. 73–77 (1974).
ICI Americas Inc., "ICI Americas Products for Cosmetics and Pharmaceuticals," (1977).
Domino Sugar Corporation, "Co–crystallization".
Kurmann et al., "Bifidobacteria in Foods", pp. 374–378 in *Encyclopedia of Food Science, Food Technology and Nutrition*, McRae et al., eds., Academic Press, New York (1993).
Hughes et al., "Bifidobacteria: Their Potential For Use In American Dairy Products", pp. 74–81 in *Food Technology* (Apr. 1991).

Primary Examiner—Leon B. Lankford, Jr.
Assistant Examiner—Francisco C. Prats
Attorney, Agent, or Firm—Hoffmann & Baron; John F. Levis

[57] ABSTRACT

The invention provides a method for preparation of a bifidobacteria-nourishing medium by subjecting a saccharide-based feedstock containing fructosyl units to flash flow conditions. The resulting shearform matrix is then treated to provide a medium having fructosyl-containing oligosaccharide. Preferably, the shearform matrix is treated by subjecting it to acid thermolysis conditions. Also provided is a method of nourishing mammalian alimentary tract for preferential growth of bifidobacteria. In addition, there is provided a medium for nourishing bifidobacteria and comestible products made therefrom.

37 Claims, No Drawings

U.S. PATENT DOCUMENTS

| | | | |
|---|---|---|---|
| 3,676,148 | 7/1972 | De Weese et al. | 426/576 |
| 3,686,000 | 8/1972 | Lawrence . | |
| 3,723,134 | 3/1973 | Chivers | 426/660 |
| 3,762,846 | 10/1973 | Chivers | 425/7 |
| 3,766,165 | 10/1973 | Rennhard | 536/123.1 |
| 3,856,443 | 12/1974 | Salvi | 425/9 |
| 3,875,300 | 4/1975 | Homm et al. | 424/433 |
| 3,876,794 | 4/1975 | Rennhard | 426/548 |
| 3,925,525 | 12/1975 | LaNieve | 264/207 |
| 3,930,043 | 12/1975 | Warning et al. | 426/515 |
| 3,951,821 | 4/1976 | Davidson | 252/1 |
| 3,967,623 | 7/1976 | Butterworth et al. | 604/370 |
| 3,972,725 | 8/1976 | Nicol | 127/58 |
| 3,981,739 | 9/1976 | Dmitrovsky et al. | 127/60 |
| 3,992,265 | 11/1976 | Hansen | 435/300 |
| 4,056,364 | 11/1977 | Dmitrovsky et al. | 422/253 |
| 4,086,418 | 4/1978 | Turbak et al. | 536/30 |
| 4,090,920 | 5/1978 | Studer, Jr. | 435/300 |
| 4,136,145 | 1/1979 | Fuchs et al. | 264/164 |
| 4,153,512 | 5/1979 | Messner et al. | 435/33 |
| 4,159,210 | 6/1979 | Chen et al. | 127/29 |
| 4,293,570 | 10/1981 | Vadasz | 426/3 |
| 4,298,619 | 11/1981 | Mutai et al. | 426/43 |
| 4,303,684 | 12/1981 | Pitchon et al. | 426/312 |
| 4,338,350 | 7/1982 | Chen et al. | 426/658 |
| 4,348,420 | 9/1982 | Lynch et al. | 426/272 |
| 4,362,757 | 12/1982 | Chen et al. | 426/599 |
| 4,371,516 | 2/1983 | Gregory et al. | 424/485 |
| 4,376,743 | 3/1983 | Dees | 264/103 |
| 4,382,967 | 5/1983 | Koshida et al. | 426/96 |
| 4,492,685 | 1/1985 | Keith et al. | 424/78.06 |
| 4,496,592 | 1/1985 | Kuwahara et al. | 426/5 |
| 4,500,546 | 2/1985 | Turbak et al. | 514/781 |
| 4,511,584 | 4/1985 | Percel et al. | 426/88 |
| 4,526,525 | 7/1985 | Oiso et al. | 425/9 |
| 4,585,797 | 4/1986 | Cioca | 514/773 |
| 4,619,833 | 10/1986 | Anderson | 426/548 |
| 4,772,477 | 9/1988 | Weiss et al. | 426/99 |
| 4,793,782 | 12/1988 | Sullivan | 425/7 |
| 4,816,283 | 3/1989 | Wave et al. | 426/565 |
| 4,853,243 | 8/1989 | Kahn et al. | 426/564 |
| 4,855,326 | 8/1989 | Fuisz | 514/777 |
| 4,872,821 | 10/1989 | Weiss | 425/9 |
| 4,873,085 | 10/1989 | Fuisz | 424/400 |
| 4,879,108 | 11/1989 | Yang et al. | 424/440 |
| 4,885,281 | 12/1989 | Hanstein et al. | 514/53 |
| 4,978,537 | 12/1990 | Song | 426/5 |
| 4,988,529 | 1/1991 | Nakaya et al. | 426/569 |
| 4,997,856 | 3/1991 | Fuisz | 514/777 |
| 5,011,532 | 4/1991 | Fuisz | 106/215 |
| 5,028,632 | 7/1991 | Fuisz | 514/772 |
| 5,034,421 | 7/1991 | Fuisz | 514/772 |
| 5,073,387 | 12/1991 | Whistler | 426/7 |
| 5,077,076 | 12/1991 | Gonsalves et al. | 426/565 |
| 5,082,682 | 1/1992 | Peterson | 426/564 |
| 5,082,684 | 1/1992 | Fung | 426/602 |
| 5,084,295 | 1/1992 | Whelan et al. | 426/565 |
| 5,089,606 | 2/1992 | Cole et al. | 536/54 |
| 5,094,872 | 3/1992 | Furcsik et al. | 426/578 |
| 5,096,492 | 3/1992 | Fuisz | 106/215 |
| 5,104,674 | 4/1992 | Chen et al. | 426/573 |
| 5,110,614 | 5/1992 | Corbin et al. | 426/555 |
| 5,206,355 | 4/1993 | Richards et al. | 536/4.1 |
| 5,236,734 | 8/1993 | Fuisz | 426/641 |
| 5,279,849 | 1/1994 | Fuisz | 426/658 |
| 5,318,794 | 6/1994 | Richards | 426/658 |
| 5,348,758 | 9/1994 | Fuisz et al. | 426/660 |

PREPARATION OF OLIGOSACCHARIDES AND PRODUCTS THEREFROM

This application is a continuation of application Ser. No. 08/282,807, filed on Jul. 29, 1994 now abandoned.

The present invention relates to a method for the preparation of sucrose-derived oligosaccharides. More particularly, it is directed to an improved method for the preparation of a composition comprising an oligosaccharide such as 1-kestose, 6-kestose, neokestose, fructooligosaccharides, difructose dianhydrides, and fructoglucans.

Sucrose-derived oligosaccharides are of considerable scientific and commercial interest in the food, pharmaceutical, feed, and nutritional products industries. They are useful as low calorie food sweeteners, nutritional supplements, and bulking agents. Moreover, researchers have reported that sucrose-derived oligosaccharides may be used as a diet supplement to support the growth of bifidobacteria.

Bifidobacteria (Bifidobacterium spp.) are non-motile, Gram positive organisms. They are natural inhabitants of the gut of humans and other warm-blooded animals. In infants, bifidobacteria are the largest group of organisms colonizing the large intestine. These organisms have a high specificity for oligofructoses and kestoses due mainly to their secretion of βD-fructofuranosidase (invertase). They play a significant role in controlling the pH of the large intestine through secretion of lactic and acetic acids, which in turn restricts the growth of potential pathogenic and putrefactive bacteria. Bifidobacteria also improve lactose-tolerance and the digestibility of milk products. Reduction in the populations of bifidobacteria is a cause of infant diarrhea. A number of the benefits of bifidobacteria for human and animal nutrition and health are described in Hughes et al. *Food Technology*, pp. 74–81 (April, 1991).

Bifidobacteria are unique in that they metabolize, and are stimulated by the presence of, oligosaccharides containing D-fructosyl units, more specifically, 1-kestose, 6-kestose, neokestose, and fructooligosaccharides;. The use of such sucrose-derived oligosaccharides as feed additives are reported to provide enhanced weight gain in poultry, swine, and other animals.

U.S. Pat. No. 5,206,355, the disclosure of which is expressly incorporated herein by reference, describes and claims a method for the production of fructoglucan polymers by the pyrolysis of amorphous sucrose in the presence of an acid catalyst. The amorphous sucrose starting material for that process is prepared by dehydrating concentrated aqueous solutions of sucrose. The nature of the sucrose is such that the presence of water during pyrolysis results in sucrose hydrolysis. It is necessary, therefore, to remove all water from the acid-sucrose melt prior to initiating the pyrolytic polymerization. The need to form sucrose solutions and thereafter to remove the water used in the process results in increased costs of energy and labor while lengthening the time of production. There exists a need for a more cost-efficient, commercially feasible process for producing sucrose-based oligosaccharides.

It is an object of the present invention to overcome shortcomings of the procedure(s) and product(s) of the prior art, and to provide improved methods for preparing oligosaccharides and the products prepared thereby.

SUMMARY OF THE INVENTION

The present invention includes a method of preparing a bifidobacteria-nourishing medium as well as the medium itself. The method includes subjecting a saccharide-based feedstock, preferably sucrose, which has fructosyl units contained therein to flash flow processing to provide a substantially amorphous shearform matrix. The substantially amorphous shearform product is then treated to provide a fructosyl-containing oligosaccharide.

In a preferred embodiment of the invention, the method of treating the shearform matrix is by acid thermolysis. As used herein, acid thermolysis relates to a process of treating saccharide-containing shearform matrix in which the shearform matrix, together with an acid catalyst, is exposed to thermal conditions conducive to reaction of the saccharides in the matrix to provide a fructosyl-containing oligosaccharide. The acid catalyst used in the reaction can be added to the saccharide-based feedstock before flash flow processing so that the acid is "carried" in the matrix. The acid catalyst can also be combined with the shearform matrix after flash flow processing. The acid catalyst is preferably a food grade acid, e.g., citric acid.

The acid thermolysis reaction referred to in the previous paragraph can be conducted by forming a melt of the shearform matrix and catalyst, and subjecting the melt to temperature conditions of from about 80° C. to about 174° C. In another type of acid thermolysis reaction, the shearform matrix and acid catalyst is subjected to conditions favoring polymerization, which include a temperature at a range of from about 110° C. to about 174° C., more preferably at a temperature of from about 125° C. to about 145° C.

Another embodiment of the present invention includes the ability to add crystalline sucrose to the melt formed during the thermolysis reaction (additional acid catalyst can be added if necessary). This embodiment enables the artisan to produce the medium in a continuous process.

Another embodiment of the present invention includes the addition of a medicament to the medium. The medicament can be added before or after flash flow processing. In one preferred embodiment, the medicament is an antibiotic.

In yet a further embodiment of the present invention, a microbial can be added to the medium. The combined medium having the shearform matrix and the microbial component can then be subjected to bacteriostatic storage conditions in order to maintain the activity and viability of the microbial. In yet a further manifestation of this embodiment, the shearform matrix which has already been subjected to flash flow processing and treated can be subjected once again to flash flow processing to provide a substantially amorphous derivative shearform matrix which can be treated and combined with the microbial component. This twice-treated matrix material and microbial can once again be subjected to flash flow processing.

Microbial components contemplated for use in the present invention includes bacteria of the genus Bifidobacterium. Also, at least one additional beneficial bacteria, such as a lactic acid bacterium, can be included in the medium.

The medium resulting from the method of preparing the present invention can then be used to treat mammals, especially humans. This method is intended to preferentially grow bifidobacteria in the alimentary tract of mammal. A product which is ideally suited for such a medium is an infant formula. Dairy products are also ideally suited for inclusion of the inventive medium. Improved dairy products such as yogurt, kefir, and fermented milk products can be made as a result of the new medium.

As a result of the present invention, mammals can be treated with a new fructosyl-containing oligosaccharide medium which improves the balance of the microflora in the alimentary tract. This is achieved by the selective growth of bifidobacteria in the tract.

As a result of the present invention, prior art procedures for preparing fructoglucan polymers from sucrose, which have high energy requirements (such as those disclosed in U.S. Pat. No. 5,206,355), have been significantly improved. Since the present invention utilizes essentially moisture-free shearform matrix material, there is no need to drive off water required to form amorphous sugar.

Additional objects, features, and advantages of the invention will become apparent to those skilled in the art upon consideration of the following detailed description of the preferred embodiments exemplifying the best mode of carrying out the present invention. However, it is not intended that the scope of coverage of the present invention is to be in any way restricted by the following detailed description and examples.

DETAILED DESCRIPTION OF THE INVENTION

The present invention is a unique medium for selectively nourishing bifidobacteria in the alimentary tract of mammals. The process of preparing the novel medium is also part of the present invention. The inventive method and resulting medium include the use of shearform matrix prepared by flash flow processing a saccharide-based feedstock which has fructosyl units contained therein.

Flash flow processing can be accomplished several ways. Flash-heat and flash-shear are two processes which can be used. In the flash-heat process the feedstock material is heated sufficiently to create an internal flow condition which permits part of the feedstock to move at subparticle level with respect to the rest of the mass and exit openings provided in the perimeter of a spinning head. The centrifugal force created in the spinning head flings the flowing feedstock material outwardly from the head so that it reforms with a changed structure. The force necessary to separate and discharge flowable feedstock is centrifugal force which is produced by the spinning head.

One preferred apparatus for implementing a flash heat process is a "cotton candy" fabricating type of machine. The spinning machine used to achieve a flash-heat condition is a cotton candy machine such as the Econo-Floss Model 3017 manufactured by Gold Medal Products Company of Cincinnati, Ohio. Any other apparatus or physical process which provides similar forces and temperature gradient conditions can also be used.

In the flash-shear process, a shearform matrix is formed by raising the temperature in the feedstock material which includes a non-solubilized carrier, such as a saccharide-based material until the carrier undergoes internal flow upon application of a fluid shear force. The feedstock is advanced and ejected while in internal flow condition, and subjected to disruptive fluid shear force to form multiple parts or masses which have a morphology different from that of the original feedstock.

The multiple masses are cooled substantially immediately after contact with the fluid shear force and are permitted to continue in a free-flow condition until solidified.

The flash shear process can be carried out in an apparatus which has means for increasing the temperature of a non-solubilized feedstock and means for simultaneously advancing it for ejection. A multiple heating zone twin screw extruder can be used for increasing the temperature of the non-solubilized feedstock. A second element of the apparatus is an ejector which provides the feedstock in a condition for shearing. The ejector is in fluid communication with the means for increasing the temperature and is arranged at a point to receive the feedstock while it is in internal flow condition. The ejector is preferably a nozzle which provides high pressure ejection of the feedstock material. See co-pending commonly-owned U.S. patent application Ser. No. 965,804 filed Oct. 23, 1992 entitled "Process For Making Shearform Matrix," which is incorporated herein by reference.

The saccharide-based feedstock used in the present invention must contain fructosyl units therein in order that the resulting medium will have fructosyl-containing oligosaccharides. The feedstock generally contains a carrier material which in the present invention can be the saccharide-based material. This material must be capable of undergoing both physical and/or chemical changes associated with flash flow processing. It has been found that sucrose is one of the most advantageous feedstocks for use in the present invention. Other materials which can be used in combination with sucrose include fructose, raffinose, stachyose, etc. In any event, the shearform matrix used in the present invention is substantially amorphous after having undergone flash flow processing.

Shearform matrix used in the present invention is essentially anhydrous as formed. That is to say the matrix contains less than 5% moisture, and usually less than about 2% after processing. This unique material offers significant improvement over the procedures presently used to produce fructoglucans, since the state of the art requires forming a sugar solution to achieve amorphousness. Consequently, the water required to form the solution must be driven off. There is no such requirement when using shearform matrix.

The next step of the present invention is an acid catalyzed thermolysis reaction. The fructosyl-containing shearform matrix is subjected to conditions of thermolysis in the presence of an acid catalyst. The acid catalyst can be combined with the shearform matrix after being subjected to flash flow processing, or can be included with the feedstock before flash flow processing. Acid catalysts useful in the present invention are primarily food grade acids which can include, but are not limited to, citric acid, tartaric acid, benzoic acid, lactic acid, disodium hydrogen phosphate, dipotassium hydrogen phosphate, sodium dihydrogen phosphate, potassium dihydrogen phosphate, phosphoric acid, phosphate buffers, and mixtures thereof. One particularly ideal acid catalyst is citric acid.

In the prior art practice of making media containing sucrose, crystalline sucrose is melted at temperatures above 180° C. It is known, however, that the thermal degradation of sucrose occurs at temperatures of from 174° C. to 186° C. and that melts formed at these temperatures contain a variety of thermal degradation products. Such degradation is commonly associated with caramelization. It is among the advantages of the use of sucrose subjected to flash flow processing conditions that sucrose melts may be obtained at temperatures substantially below the degradation temperature of crystalline sucrose, resulting in fewer thermal degradation by-products being formed. Instead, the formation of melts using shearform matrix produced from sucrose-containing feedstock results in rearrangements of the saccharide moieties producing fructosyl-containing oligosaccharides.

Moreover, it has also been shown that, by use of the present invention, melted shearform matrix prepared from sugar can be used to reduce the temperature of formation of additional melt from crystalline sucrose. In fact, Example 2 clearly demonstrates this unique and unexpected characteristic. As a result of this feature, crystalline sugar has been shown to reduce to an amorphous melt at about 145° C., well below the temperatures which cause unwanted thermal degradation products. As an additional feature, this ability to reduce melt formation temperature enables the manufacturer to employ a continuous process to prepare fructosyl-containing oligosaccharides.

It will also be noted that thermal degradation is partially dependent upon the time at which a melt is maintained at a temperature capable of inducing such degradation. The practice of continuous melt processes has traditionally required high temperature treatment for longer periods. In contrast, the fructosyl-containing oligosaccharide medium of the invention can be produced in a continuous process at a substantially lower temperature. Thus, the melt can be maintained for extended times.

Accordingly, the method of the invention enables the skilled artisan to produce fructosyl-containing oligosaccharide media, which are substantially free of saccharide degradation products, at temperatures of from about 80° C. to about 174° C. At a temperature of from about 80° C. to about 110° C., it is believed that less energetic rearrangements are favored, resulting in a reaction product having relatively smaller fructosyl-containing oligosaccharides. Alternatively, the shearform matrix and acid catalyst can be subjected to conditions which favor polymerization of the matrix to yield a reaction product which contains fructosyl-containing oligosaccharides. The conditions favoring polymerization include a temperature of from about 110° C. to about 174° C. A preferred temperature range is from about 125° C. to about 145° C., more preferably about 135° C.

In yet a further embodiment of the present invention, the medium can include medicinal substances. A non-limiting list of such substances is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psychotropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and anti-thyroid preparations, diuretics, anti-spasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

Preferably, the medicament is an antibiotic. The medicament can be included in the medium after the formation of the shearform matrix, or can be included in the feedstock before flash flow processing.

In yet a further embodiment of the present invention, a microbial component can be added to the medium either before or after flash flow processing or in subsequent flash flow processing products. Since the target bacteria are bifidobacteria, one of the preferred microbial components includes bacteria of the genus Bifidobacterium. The bifidobacterium can be selected from one species selected from the group consisting of *Bifidobacterium bifidum, Bif. infantis, Bif. breve, Bif. longum, Bif. adolescentis, Bif. angulatum, Bif. catenulatum, Bif. pseudocatenulatum, Bif. dentium*, and mixtures thereof. The present invention can also contain a microbial component selected from one of the beneficial bacteria such as a lactic acid bacterium. One such bacterium is a Lactobacillus.

Comestible products may be prepared from the present medium, especially dry infant formula products, and dairy products such as yogurt, kefir, fermented milk products, etc. An overview of various bifidus enhanced foods is provided in an article entitled "Bifidobacteria in Foods" at pages 374–378 in *Encyclopedia of Food Science, Food Technology and Nutrition*, Macrae et al., eds., Academic Press, New York (1993).

Preferred Embodiments

In accordance with the present invention there has been provided a product resulting from pyrolyzing sucrose to produce a mixture which includes a fructosyl-containing oligosaccharide such as 1-kestose, 6-kestose, neokestose, fructooligosaccharides, and difructose dianhydrides. The method includes forming a melt of amorphous shearform product and an acid catalyst by heating at a temperature of from about 80° C. to about 174° C. The sucrose melt forms readily at a relatively low temperature which is below the melting point of sugar. Conventional melts of crystalline sucrose must be formed at much higher temperatures, e.g., above about 174° C., resulting in a wide variety of undesirable thermal degradation products. Moreover, crystalline sucrose can be added (with additional catalysts if necessary) to the melt to increase the amount of reactant for the thermolysis reaction. Additional acid catalyst can be added to the melt with crystalline sucrose to maintain the acid:sucrose ratio and to aid in the pyrolytic conversion. Reference is made to U.S. Pat. No. 5,206,355 for a detailed description of the chemical formulas and means and manner for isolation and identification of the resulting products formed by the method of the present invention.

Furthermore, a continuous process can be employed in preparing the medium of the present of the invention by forming the thermolytic reaction mixture and continuing to add crystalline sucrose and acid catalyst. Preferably, the continuous process is conducted in a jacketed extruder in which amorphous sucrose (resulting from the flash flow processing) and food acceptable acids are fed into the heated extruder to form a zone of molten acidified amorphous sucrose along the length of the extruder. A blend of crystalline sucrose and food acceptable acid can be fed continuously at a point along the extruder as the polymerized product is forced to the exit end. The reaction is controlled by controlling melt zone temperature and residence time (feed rate) of crystalline sucrose into the molten amorphous reaction mixture present in the extruder. It has been found that the amount of catalyst employed in the melt of the present invention typically ranges from about 0.2% to about 5.0% by weight based on the amount of amorphous matrix. Preferably, the catalyst is present in the composition at about 1% by weight of the sucrose (or equivalent) component.

The method of the invention provides media containing fructosyl-containing oligosaccharides. As used herein the term "fructosyl-containing oligosaccharide" is meant to include rearrangement products resulting from treating a shearform matrix according to the method of the invention. Such products include, without limitation: 1-kestose, 6-kestose, neokestose, fructooligosaccharides, difructose dianhydrides, fructosans, fructoglucans, and mixtures thereof.

The oligosaccharide product distribution produced in accordance with the present method is dependent upon both the temperature of the melt and the time period the melt is held at that temperature. The melt can be heated to a temperature of up to 80° C. to 174° C., more typically from 135° C. to about 170° C., and most preferably at about 135° C. for from about 5–60 minutes.

EXAMPLE 1

Substantially amorphous shearform matrix material was prepared by subjecting sucrose to flash heat processing in a standard cotton candy spinning machine. Citric acid (1% by weight) was mixed with the shearform material and heated to about 135° C. to yield a thick melt. The melt was held at the temperature of from about 145° C. to about 170° C. for about 5–60 minutes.

The melt solidified to a glass as it cooled to a temperature of about 25° C. Chromatographic analysis of the resultant product indicated the presence of sucrose, glucose, fructose, difructose dianhydrides, 1-kestose, 6-kestose and neokestose.

The glass can be added to conventional foods or prepared for delivery directly to a human to enhance the viability and activity of bifidobacteria present in the alimentary tract. Moreover, medicaments and/or microbials, such as bifidobacteria, etc. can be added to the product resulting from Example 1.

EXAMPLE 2

Sucrose derived oligosaccharides were prepared by rapidly melting approximately 200 grams of amorphous shearform sucrose based product and approximately 2 grams of powdered anhydrous citric acid at about 135° C. in a 2 liter vessel. A mixture of about 2,500 grams of crystalline sucrose and 25 grams of citric acid (1% by weight of sucrose) were then added to the melt with stirring at a rate to maintain a liquid condition. The melt was held at a temperature of about 145° C. to about 170° C. for about 5–60 minutes. The melt was allowed to cool to a temperature of about 25° C. Chromatographic analysis of the resulting product indicated the presence of sucrose, glucose, fructose, difructose dianhydrides, 1-kestose, 6-kestose and neokestose.

Similar to the product prepared in Example 1, the product prepared in Example 2 can be modified by addition of medicaments and/or microbials. The product can be fed to human subjects to improve the viability and beneficial activity of bifidobacteria in the alimentary tract.

This example clearly demonstrates the ability to prepare amorphous sucrose melt well below the temperatures at which "carmelization" and unwanted thermal degradation products are produced. The example also shows how a continuous process can be used to prepare the desired oligosaccharides.

Although the present invention has been described in such a way that those skilled in the art are able to reproduce the invention, it is believed that further modifications and changes can be made to the invention without departing from the spirit thereof and it is intended to include all such changes and modifications as come within the scope of the claims appended hereto.

What is claimed is:

1. A method of preparing a bifidobacteria-nourishing medium, comprising:

subjecting an essentially anhydrous saccharide-based feedstock having fructosyl units contained therein to flash flow processing under essentially to provide a substantially amorphous and essentially anhydrous shearform matrix, and reacting said shearform matrix with an acid catalyst under acid thermolysis conditions to provide a fructosyl-containing oligosaccharide.

2. The method of claim 1, wherein said acid thermolysis conditions include reacting the shearform matrix with an acid catalyst.

3. The method of claim 2, wherein the acid catalyst is carried in the saccharide-based feedstock prior to flash flow processing.

4. The method of claim 2, wherein the acid catalyst is added to the shearform matrix after flash flow processing.

5. The method of claim 2, wherein said acid catalyst is a food acceptable acid.

6. The method of claim 5, wherein said food acceptable acid is selected from the group consisting of citric acid, tartaric acid, benzoic acid, lactic acid, disodium hydrogen phosphate, dipotassium hydrogen phosphate, sodium dihydrogen phosphate, potassium dihydrogen phosphate, phosphoric acid, phosphate buffers, and mixtures thereof.

7. The method of claim 5, wherein said food acceptable acid is citric acid.

8. The method of claim 1, wherein said conditions comprise a temperature of from about 80° C. to about 174° C.

9. The method of claim 8, wherein said conditions comprise a temperature of from about 110° C. to about 174° C.

10. The method of claim 9, wherein said conditions comprise a temperature of from about 125° C. to about 145° C.

11. The method of claim 1, further comprising adding crystalline sucrose to the melt formed during said thermolysis.

12. The method of claim 11, further comprising adding crystalline sucrose and additional acid catalyst to said melt.

13. The method of claim 11, wherein said method is continuous.

14. The method of claim 1, wherein said method further comprises providing a medicament in said medium.

15. The method of claim 14, wherein said medicament comprises an antibiotic.

16. The method of claim 1, wherein said saccharide-based feedstock comprises sucrose.

17. The method of claim 16, wherein said saccharide-based feedstock further comprises fructose.

18. The method of claim 16, wherein said saccharide-based feedstock further comprises a compound selected from the group consisting of raffinose, stachyose, and mixtures thereof.

19. The method of claim 1, further comprising the step of combining said shearform matrix with a microbial component comprising bifidobacteria.

20. The method of claim 19, wherein said microbial component includes at least one species selected from the group consisting of *Bifidobacterium bifidum, Bif. infantis, Bif. breve, Bif. longum, Bif. adolescentis, Bif. angulatum, Bif. catenulatum, Bif. pseudocatenulatum, Bif. dentium*, and mixtures thereof.

21. The method of claim 19, wherein said microbial component further includes at least one additional bacterium.

22. The method of claim 21, wherein said additional bacterium is a lactic acid bacterium.

23. The method of claim 22, wherein said lactic acid bacterium is a Lactobacillus.

24. The method of claim 19, further comprising the step of subjecting said combined treated shearform matrix and microbial component to bacteriostatic storage conditions.

25. The method of claim 1, further comprising subjecting said treated shearform matrix to flash flow processing to provide a substantially amorphous derivative shearform matrix.

26. The method of claim 25, further comprising combining said derivative shearform matrix with a microbial component.

27. A method of nourishing mammalian alimentary tract for preferential growth of bifidobacteria, comprising:

(a) reacting a saccharide-based, substantially amorphous and essentially anhydrous shearform matrix having fructosyl units contained therein with an acid catalyst under acid thermolysis conditions to provide a fructosyl-containing oligosaccharide, and (b) introducing to said alimentary tract bifidobacteria-nourishing medium prepared from said fructosyl-containing oligosaccharide.

28. The method of claim 27, wherein said medium further comprises a medicament.

29. The method of claim 28, wherein said medicament comprises an antibiotic.

30. The method of claim 27, wherein said medium further comprises a microbial component comprising bifidobacteria.

31. The method of claim 30, wherein said microbial component includes at least one species selected from the group consisting of *Bifidobacterium bifidum, Bif. infantis, Bif. breve, Bif. longum, Bif. adolescentis, Bif. angulatum, Bif. catenulatum, Bif. pseudocatenulatum, Bif. dentium*, and mixtures thereof.

32. The method of claim 30, wherein said microbial component further includes at least one additional bacterium.

33. The method of claim 32, wherein said additional bacterium is a lactic acid bacterium.

34. The method of claim 33, wherein said lactic acid bacterium is a Lactobacillus.

35. The method of claim 27, wherein said medium further comprises a dairy product.

36. The method of claim 35, wherein said dairy product is selected form the group consisting of yogurt, kefir and fermented milk.

37. The method of claim 35, wherein said medium comprises infant formula prepared from said shearform matrix.

* * * * *